(12) United States Patent
Gutiérrez (10) Patent No.: US 10,342,840 B2
(45) Date of Patent: Jul. 9, 2019

(54) NANOPARTICULATE TITANIUM DIOXIDE NANOMATERIAL MODIFIED WITH FUNCTIONAL GROUPS AND WITH CITRIC EXTRACTS ADSORBED ON THE SURFACE, FOR THE REMOVAL OF A WIDE RANGE OF MICROORGANISMS

(71) Applicant: Inmolecule International Limited, London (GB)

(72) Inventor: Gabriela León Gutiérrez, Col. Periodista (MX)

(73) Assignee: Inmolecule International Limited, London (GB)

( * ) Notice: Subject to any disclaimer, the term of this patent is extended or adjusted under 35 U.S.C. 154(b) by 529 days.

(21) Appl. No.: 14/899,628

(22) PCT Filed: Jun. 19, 2014

(86) PCT No.: PCT/MX2014/000094
§ 371 (c)(1),
(2) Date: Dec. 18, 2015

(87) PCT Pub. No.: WO2014/204290
PCT Pub. Date: Dec. 24, 2014

(65) Prior Publication Data
US 2016/0143981 A1    May 26, 2016

(30) Foreign Application Priority Data
Jun. 20, 2013   (MX) .................. MX/A/2013/007201

(51) Int. Cl.
*A61K 9/00*       (2006.01)
*A61K 36/752*   (2006.01)
(Continued)

(52) U.S. Cl.
CPC .............. *A61K 36/752* (2013.01); *A61K 9/16* (2013.01); *A61K 33/24* (2013.01);
(Continued)

(58) Field of Classification Search
CPC .................................................... A61K 36/752
See application file for complete search history.

(56) References Cited

U.S. PATENT DOCUMENTS 5,792,793 A   8/1998  Oda et al.
6,087,405 A   7/2000  Plecha et al.
(Continued)

FOREIGN PATENT DOCUMENTS

EP   1981513 A2   10/2008
EP   2099429 A2    9/2009
(Continued)

OTHER PUBLICATIONS

A. Maury A et al., "Surface functionalization of TiO2 with plants extracts and their combined antimicrobial activities against *E. faecalis* and *E. coli*", Journal of Research Updates in Polymer Science, 2012, vol. 1, pp. 43-51.
(Continued)

*Primary Examiner* — Paul W Dickinson
(74) *Attorney, Agent, or Firm* — Antoinette M. Tease (57) ABSTRACT

A conjugate of a titanium dioxide nanomaterial and nanoparticulate herbal and/or fruit extracts is synthesized by impregnation, using titanium dioxide as support, to which are adsorbed organic functional groups, inorganic radicals and plant extracts that confer thereon anti-microbial properties with high disinfectant and antiseptic power, removing bacteria, fungi, mycobacteria, spores, mycobacteria, protozoa and viruses. The conjugate is a solid nanomaterial in liquid suspension and is prepared by impregnation to disperse the functional groups and the extract particles, with
(Continued)

temperature control to stabilize the interactions within the network of the support. Virucidal, bactericidal, fungicidal, mycobactericidal, mycoplasmicidal, antiprotozoal and sporicidal activity of the nanoparticulate biomaterial depends on the particle size of the support oxide, the functionalization and the dispersion of extracts adsorbed on the surface. The functional groups may include hydroxyl, carboxyl, amine, sulfate, phosphate, and the supports may be titanium dioxide, silica, zirconia, zinc oxide, alumina and other metal oxides.

16 Claims, 3 Drawing Sheets

(51) Int. Cl.
| | |
|---|---|
| C01G 23/047 | (2006.01) |
| C09D 5/14 | (2006.01) |
| A61K 9/16 | (2006.01) |
| A61K 33/24 | (2019.01) |
| A61K 47/69 | (2017.01) |
| B82Y 5/00 | (2011.01) |
| B82Y 40/00 | (2011.01) |
| B82Y 30/00 | (2011.01) |

(52) U.S. Cl.
CPC ........ *A61K 47/6923* (2017.08); *C01G 23/047* (2013.01); *C09D 5/14* (2013.01); *B82Y 5/00* (2013.01); *B82Y 30/00* (2013.01); *B82Y 40/00* (2013.01)

(56) References Cited

U.S. PATENT DOCUMENTS

| | | | |
|---|---|---|---|
| 6,117,814 A | 9/2000 | Plecha et al. | |
| 8,372,382 B2 | 2/2013 | Norman | |
| 8,404,743 B2 | 3/2013 | Swanzy | |
| 2012/0225147 A1 | 9/2012 | Hines | |
| 2012/0237455 A1 | 9/2012 | Trivedi et al. | |
| 2012/0244086 A1 | 9/2012 | Trivedi et al. | |

FOREIGN PATENT DOCUMENTS

| | | |
|---|---|---|
| EP | 2448416 A1 | 5/2012 |
| EP | 2470159 A1 | 7/2012 |
| WO | 9321969 A1 | 11/1993 |
| WO | 2003064324 A2 | 8/2003 |
| WO | 2006079757 A1 | 8/2006 |
| WO | 2007084998 A2 | 7/2007 |
| WO | 2007141590 A1 | 12/2007 |
| WO | 2008070538 A2 | 6/2008 |
| WO | 2011002929 A1 | 1/2011 |
| WO | 2011026039 A1 | 3/2011 |

OTHER PUBLICATIONS

M. Sundrarajan et al., "Green synthesis of titanium dioxide nanoparticles by Nyctanthe arbor-tristis leaves extract", Chalcogenide Letters, 2011, vol. 8, No. 8, pp. 447-451.

G. Rajakumar et al., "Eclipta prostata leaf aqueous extract mediated synthesis of titanium dioxide nanoparticles", Materials Letters, 2012, vol. 68, pp. 115-117.

G. Rajakumar et al., "Fungus-mediated biosynthesis and characterization of TiO2 nanoparticles and their activity against pathogenic bacteria", Spectrochimica Acta Part A, 2012, vol. 91, pp. 23-29.

K. S. Jamuna et al., "Nano-scale preparation of titanium dioxide by Desmodium gangeticum root aqueous extract", Ceramics International, 2014 [accessible in line Apr. 18, 2014], vol. 40, pp. 11933-11940.

D. Mubarakali et al., "Plant extract mediated synthesis of silver and gold nanoparticles and its antibacterial activity against clinically isolated pathogens", Colloids and Surfaces B: Biointerfaces, 2011, vol. 85, pp. 360-365.

NANOPARTICULATE TITANIUM DIOXIDE NANOMATERIAL MODIFIED WITH FUNCTIONAL GROUPS AND WITH CITRIC EXTRACTS ADSORBED ON THE SURFACE, FOR THE REMOVAL OF A WIDE RANGE OF MICROORGANISMS

FIELD OF THE INVENTION

The present invention relates to the synthesis and preparation of a mixture of herbal and fruit extracts, and its absorption on titanium dioxide nanomaterial modified with functional groups, with a general formulation of $E/M_aO_{2(c)}(OH)_v(PO_4)_w(SO_4)_xCl_y(NH_2)_z$, where E is a complex solution obtained from grapefruit, lemon, tangerine, and other citrus extracts, and M is titanium. The matrix particle size, acidity, matrix mean pore size and particle size are controlled during synthesis. The nanomaterial of the present invention is used to inactivate viruses, remove bacteria, mycobacteria, fungi and spores. The invention is intended to the use of these nanoparticles for disinfection and sanitizing of biological surfaces and is not limited to a specific application field.

BACKGROUND ART

From the beginning of times, human beings have tried to alter matter, and recently, scientists have acquired the ability to manipulate matter, the scientist ability to manipulate materials at atomic and molecular scale through the use of nanotechnology has evolved from science fiction to science reality in common life. Today, nanotechnology is being developed in order to prevent, diagnose and treat infectious diseases, with some products about to enter the clinical trial phase. Advances in this field are exponential (1-6). Interdisciplinary nanoscience and researches including chemists, physicists, biologists and engineers are concerned on the necessity of developing ecological and sustainable methods for the synthesis of nanomaterials. There is a trend of excitement to integrate green chemistry approaches in the design of environmentally benign materials and processes. Quick advances are taking place in the synthesis of biocompatible mixed oxides or metallic nanomaterials and single bimetallic oxides, as well as the surface modification thereof intended for bioactivity and nanomedicine applications. Biosynthesis of nanoparticles as an emerging ending point from nanotechnology and biotechnology interaction has been increasingly drawing attention due to the increasing necessity to develop environmentally friendly technologies regarding material synthesis. Biomolecules as reagents have been found to have a significant advantage over equivalent molecules as protective agents (7-13).

Materials properties can change notably when their particle size is reduced to a nanometer scale. In materials science "particle" is a general term for describing small solid objects having sizes ranging from the atomic scale ($10^{-10}$ m) to microscopic scale ($10^{-3}$ m). However, particle size is often found between $10^{-9}$ to $10^{-3}$ m. Large particles ($>10^{-6}$ m) are commonly called grains (i.e. zeolites, carbon, Raney metals) and small particles (<15 nm) of mixed (metal) oxides, i.e. $TiO_2$—$SiO_2$, $TiO_2$ or $SiO_2$ are often added (14-20). All the materials consist of grains (particles) formed by agglomeration of nanoparticles.

In conventional materials, grains have a sized comprised between 100 micrometers and millimeters (mm), while nanomaterial particles are within the range of a billionth of a meter ($10^{-9}$). The mean diameter of human hair is approximately one nanometer. The radius of an atom is 1 to 3 Angstrom (Å), and one nanometer is equal to 10 Å. Nanomaterials are solid, rigid, resistant and ductile at high temperatures, they are resistant to degradation, erosion and corrosion, as well as chemically very active. The physical and chemical properties of each nanomaterial or nanoparticle material are determined by the type of compounds and the interactions by which nanoparticles are functionalized; thus electron density and hydroxyl concentration in the network has an important role in the rupture of pathogenic DNA.

One of the areas where the importance of nanoparticles has increased is the disinfection field, where a particle distribution having well defined shape and size will be obtained in order to improve disinfection activity. In particular, it is necessary to obtain highly dispersed particles where most of the atoms are located on the surface. The structure includes a solid area, pore size, as well as shape and volume of pores. These parameters are also important, since they are responsible for increasing the microorganism disinfection rate. The adsorption of functional groups on the surface makes them selective to pathogenic microorganisms and the adsorption of citrus extracts confers them disinfectant power.

Although the activity can be directly related to the total contact area between the material and the organism, determination of the surface is considered an important requirement in the characterization of said material. Also, it is necessary to specify the nature of pore structure since it is responsible for controlling the transport of reagents and products.

Figure 2:
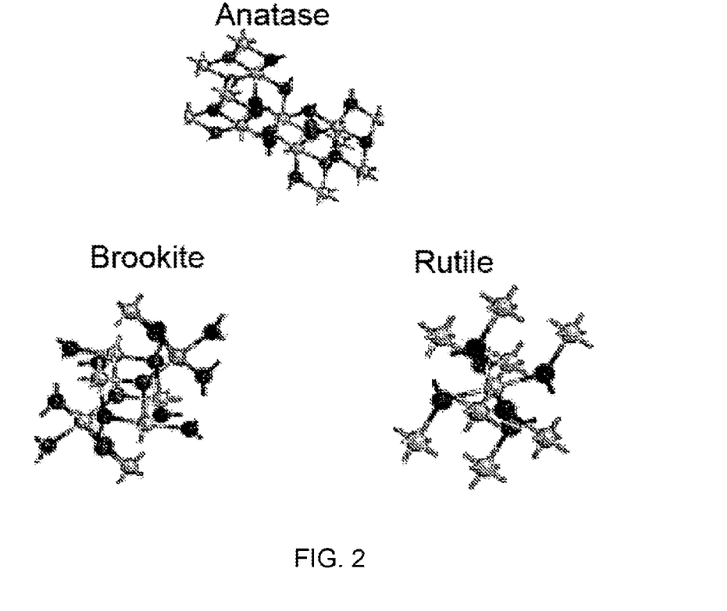
FIG. 2. Crystalline phases of titanium dioxide.

Titanium dioxide can be found naturally in three crystalline phases: anatase, rutile, and brookite (FIG. 2). Anatase and brookite can transform into rutile at high temperatures. Anatase can irreversibly transform into rutile by heating. Several factors contribute in phase shifting, such as particle size, crystal morphology, but in particular, the influence of ions on network poisoning. Literature cites one of the three phases, anatase, as having high chemical stability and corrosion resistance, being inert to biological agents and having high specific surface area. However, the commercial titanium oxide is a mixture (Degussa P25) containing 60 to 80% anatase. The only problem in obtaining anatase is that rutile is thermodynamically more stable. Anatase and rutile structures are tetrahedral, while brookite is orthorhombic, each titanium atom is bonded to 6 almost equally distant oxygen atoms, and each oxygen atom is bonded to three titanium atoms.

The need for disinfectants and antiseptics having specific action to inactivate virus and kill bacteria, mycobacteria, mycoplasma, fungi, protozoa and spores with proven high efficiency against these and other microorganisms has increased.

This has a relationship with the increase in new infections (e.g. HIV, influenza and avian flu) and the re-emergence of previously controlled infections due to drug resistance, environmental changes and lifestyle alterations. Besides, the use of novel medical devices, which cannot be sterilized through conventional techniques, such as heat treatment, can spread some infectious diseases. Nanotechnology will have a deep impact on nosocomial infections and the diseases caused thereby, for improved diagnosis, prevention and detection, directed therapies, and antibacterial, antiviral, antimycotical, antimycobacterial and sporicidal materials. According to literature, antimycobacterial activity is closely linked to sporicidal activity mainly around the *Bacillus Subtilis*.

Diagnosis technologies combine a recognition system and a detection system, comprising a small cantilever that moves over the antigen-binding site with nanowires detecting current of cell binding immunity.

For prevention, nanotechnology-based microbicides are tested against HIV and other viruses, and are now in early clinical trials. Laboratory studies on new vaccines against hepatitis B, tuberculosis, HIV, influenza and antibacterial surface coatings or materials, including those for the medical sector, look promising. These coatings can reduce the problem related to bacteria or virus adherence to hospital surfaces and have a beneficial impact on intrahospital transmission of multiresistant bacteria, virus, spores, fungi, etc., which is a serious problem not yet solved. Titanium dioxide has a specific interaction with many biological molecules, microbes, algae, cells and living tissues. Specific interactions mean that they are different from common reactions between non-viable materials and biomolecules or living tissues. Interactions are mostly beneficial from the point of view of biotechnology applications. Titanium dioxide is known to form a direct bond with living tissues that can be used in biomaterials applications. Other application fields of the titanium dioxide include biosensors, tissue engineering, genus therapy, controlled delivery of therapeutic agents, and environmental protection (21-30).

Microbial safety is still a significant concern in priority health topics, regulatory organizations, and industries around the world. Traditionally, many strategies have been used to control microorganisms. Although synthetic antimicrobials are approved in many countries, recent trends have been towards the use of natural products, which requires exploration of safe, effective and acceptable antimicrobials from alternative sources.

In recent years nanoparticle assembly for disinfection of viral particles, virus-cell interactions, and viral pathogenesis, have taken into account these approaches for the development and design of new strategies. The rotavirus is a genus of double-stranded RNA virus in the family Reoviride (double-stranded (ds)). RNA viruses are a diverse group of viruses with a wide range of hosts (humans, animals, plants, fungi and bacteria), genome segment, organization and number (one to twelve), and virion (T number, capsidae layers or turrets).

Influenza, commonly known as flu, is an infectious disease caused by ARN viruses. The type A influenza virus particle or virion is about 80-120 nm in diameter and generally approximately spherical, although filamentous shapes can occur. Unusually for a virus, the influenza type A virus genome is not a single piece of nucleic acid, but a segmented eight-pieces of antisense RNA (13.5 kilobases total), encoding 11 proteins (HA, NA, NP, M1, M2, NS1, NEP, PA, PB1, PB1-F2, PB2). The best features of these viral proteins are hemagglutinin and neuraminidase, two large glycoproteins found on the outside of viral particles. Functionalized nanoparticulate biocatalysts of the present patent break ARN bonds and protein structure of this type of virus.

Extracts

Plants contain numerous components and constitute valuable sources of novel biologically active molecules having antimicrobial properties. Said components are extracted from certain plants either as standardized extracts or as a source of pure compounds, providing unlimited opportunities for control of microbial proliferation due to its chemical diversity. Many plant extracts have antimicrobial activity against various bacteria, yeasts and molds, but variations in quality and quantity of bioactive components are significant drawbacks. The development of effective isolation procedures that produce standardized extracts, as well as the safety and toxicology assessment of said antimicrobials require further research (45-47).

Antimicrobial properties of essential oils (EOs) have been acknowledged for centuries and with the increasing demand for changes in consumer trends, legislation and isolation of antibiotic-resistant pathogenic agents, alternatives to chemical products based on bactericides must be found. Citrus oils are not only useful in foods, but they are also generally recognized as safe (GRAS), and have been found to be inhibitory, in both oil and vapor form, against a range of both Gram-positive and Gram-negative bacteria. This group of oils can provide natural antimicrobials, which are required to meet many requirements (45-47).

STATE-OF-THE-ART PATENTS

U.S. Pat. No. 6,117,814. This patent describes a titanium oxide containing support, which also incorporates both silica and alumina as binder in the structure thereof. The purpose of said binder is to impart improved mechanical properties to the support. The support's size range is of about 20 to 120 microns. Said support comprises about 50% of binder manufactured by a sol-gel process.

U.S. Pat. No. 6,087,405. This invention describes a support for Fischer-Tropsch reaction of synthesis gas. Said support structure contains metals from Group VII. The rutile-anatase ratio within said structure is a distinctive feature of this patent.

WO/2003/064324. The invention relates to a titanium oxide-based polymer composition. The inventive composition comprises a TiOx (OH) and $(H_2O)z$ (x+y+z=3) titanium oxide-based polymer in the form of a gel or sol. Said polymer, which has a one-dimensional (1D) structure, is made from concentric fibers having a periodicity, which is deduced from the spacing between said fibers, of between 3.5 and 4. Each fiber comprises TiO6 octahedrons and each TiO6 octahedron shares two opposite edges with two adjacent octahedrons (2×2.92 Å) in order to form infinite chains that develop along the fiber's axis. According to the invention, two adjacent chains form double lines as a result of the shared edges (2×3.27 Å). The inventive polymer is suitable for use as a photosensitive element in a photovoltaic cell, such as a window sunscreen.

WO/2006/079757. Method of preparing stable oxide ceramic precursor sol-gel solutions based on lead, titanium, zirconium and lanthanide(s) and method of preparing said ceramic. The invention relates to a method of preparing a stable oxide ceramic precursor sol-gel solution based on lead, titanium, zirconium and lanthanide(s). The invention comprises the following successive steps consisting in: a) preparing a sol-gel solution by bringing a molecular lead precursor, a molecular titanium precursor, a molecular zirconium precursor and a molecular lanthanide precursor into contact with a medium comprising a diol solvent and optionally an aliphatic mono-alcohol; b) leaving the solution thus obtained to stand for a sufficient period of time in order to obtain a solution having an essentially-constant viscosity; and c) diluting the solution obtained in the preceding step with a diol solvent identical to that used in step a, or a solvent that is miscible with said solvent, at a predetermined rate. The invention can be used for preparing an oxide ceramic material comprising lead, a lanthanide metal, titanium and zirconium.

WO/2007/141590. Sol-gel nanostructured titanium oxide reservoirs for use in the controlled release of drugs in the central nervous system and method of synthesis. The invention is related to a sol-gel nanostructured titanium dioxide reservoir and its synthesis which is biocompatible with brain tissue. The pore size distribution, crystallite size and the extent of the crystalline phase distribution of anatase, rutile and brookite can be fully controlled. This device may be used to contain neurological drugs. It may be inserted directly into brain tissue for the purpose of the controlled time release of drugs over a period of from 6 months to three years. The patent uses the sol-gel method and is limited to the manufacture of particles contrary to the method of the present patent where a pre-manufactured material is used and its surface is modified by means of impregnation.

WO93/21969. Novel coating materials for biomedical applications, particularly for the use on biomedical implants, said coating material comprising gel-derived titanium oxide, wherein said material is capable of inducing calcium phosphate formation onto its surface under in vitro conditions, e.g. in a simulated body fluid and/or under in vivo conditions, processes for the preparation of the coating materials, as well as their use in biomedical implant technology.

U.S. Pat. No. 8,404,743 B2. Compounds comprising a zinc oxide complex chemically bonded to one or more molecules having an acidic hydrogen such as, for example, an organic acid. The invention further provides for compositions comprising said compounds and method for making the same.

US 2012/0244086 A1. Compositions for dental use, comprising *zingiber officinale* extract by using zinc-derived materials, with antibacterial properties.

US 2012/0237455 A1. Compositions for oral use, comprising *zizyphus joazeiro* extract by using zinc-derived materials, with antibacterial properties.

EP 1,981,513 A2. A topical skin care composition comprising kakadu plum extract or acai berry extract, or a combination of both. The composition can have a high oxygen radical absorbance capacity (ORAC) value. The composition can improve skin's visual appearance, physiological functions, clinical properties, and/or biophysical properties. Nanoparticles are not used therein, but the invention shows antibacterial properties.

US 2012/0225147 A1. A topical composition for visually improving skin appearance comprising an effective amount of *Malpighia punicifolia* (acerola), *Myrciaria dubia* (camu camu), and *Ribes nigrum* (black currant) extracts, and a dermatologically acceptable vehicle comprising water, glycerin, dimethicone or cyclomethicone, stearic acid, carbomer, and sodium hydroxide. It exhibits antibacterial properties.

EP 2,099,429 A2. Micellar nanoparticles comprising polyethylene glycol (PEG), phospholipids, cholesterols, glycolipid fatty acids, bile acids, and saponins encapsulating the botulinum toxin in order to reduce its toxic effects. They exhibit antibacterial properties.

U.S. Pat. No. 8,372,382 B2. Non-ionic oil-in water emulsion comprising less than 50% by weight of water, a combination of non-ionic emulsifiers and non-ionic emulsion stabilizers, a combination of humectant skin conditioning agents, moisturizers and a combination of UV absorbing agents. The emulsion can be stable and have an SPF of at least 30. Nanoparticles are not used therein, but the invention shows antibacterial properties.

EP 2,470,159 A1. Compositions and methods for treating skin comprising a chemically compatible combination of skin active ingredients comprising palmitoyl tetrapeptide-7, methylsilanol mannuronate, and *Lactobacillus* ferment, a chemically compatible combination of skin active ingredients comprising plant extracts from *Punica granatum, Castanea sativa, Gossypium hirsutum*, and *Euterpe oleracea*, and a dermatologically acceptable vehicle. The compositions can be substantive in that they can remain on a person's skin during sleep. Nanoparticles are not used therein, but the invention exhibits antibacterial properties.

U.S. Pat. No. 5,792,793 A. A complex formed by the coordination between a thiol group-containing compound and a silver ion; an antibacterial, antifungal, and antiviral agent containing the same as the active agent; and an antibacterial, antifungal, and antiviral agent compatible with various vehicles and carriers, sustains its activity for long, and has reduced peroral rout toxicity, skin irritation and mucosa irritation.

EP 2,448,416 A1. (Text from WO/2011/002929A1) Preservative antimicrobial compositions comprising low concentrations of botanical extracts, in synergistic combinations with alkanediols in a solvent system, optionally with fruit acids. Furthermore, the present invention relates to a preservative or antimicrobial compositions which comprise a silver compound, an essential oil or individual constituent, one or more zinc salts, and one or more alkanediol. The compositions of the invention may be used in personal care products including wound care products or in veterinary use. Preferably, the compositions of the invention have little or no human-detectable fragrance.

SUMMARY OF THE INVENTION

The main object of the present invention is the use of nanotechnology for the development of a titanium dioxide nanomaterial with herbal or fruit extracts adsorbed on the surface thereof for use in inactivating any type of virus, and killing of bacteria, fungi, mycoplasma, mycobacteria, protozoa and spores.

The optimization of said nanomaterial allowing for the control of the following parameters: support acidity, BET area, pore size distribution, particle size, functionalization extent, dispersion of adsorbed extracts onto the support is significant in order to gain a high activity to break CC and CN bonds of protein, RNA and DNA in pathogenic microorganisms. It is of significance that said matrix-supported extracts be fully dispersed all over the support so as to obtain a high cracking efficiency on protein and nucleotide CC and CN bonds.

The nanomaterial support is a nanoparticulate inorganic metal oxide functionalized through an impregnation process. Said material have been functionalized and evenly dispersed with extracts having a small particle size (0.3-10 nm).

The present invention addresses current issues of disinfectants, most of which are pollutants, irritants, toxic, non-biodegradable or even carcinogenic. Besides being selective, no harm is caused to human beings, which is a further advantage versus non-toxic disinfectants.

BRIEF DESCRIPTION OF THE FIGURES

The system is a traditional vapor entrainment system with a first vapor generating flask. With a second flask where raw materials, which will undergo extraction, are placed, and a third flask for liquid collection.

Crystalline phases of titanium dioxide: anatase, rutile and brookite. Anatase phase is meta-stable and has oxygens on the outside of the crystal.

Scan electron microscopy, where nanoparticle clusters are seen with sizes between 1 and 100 nm. Transmission microscopy showing the existence of particles≤1-2 nm.

DETAILED DESCRIPTION OF THE INVENTION

The present invention relates to the conjugate of a titanium dioxide nanomaterial with herbal and/or fruit extracts adsorbed onto the surface thereof, synthesized by means of industrial impregnation process, using nanoparticulate (1-100 nm) inorganic oxides as support. Said oxide nanoparticles are functionalized with organic functional groups, inorganic radicals and plant extracts adsorbed thereon, which provide the property of an anti-microbial agent. With such configuration, said material has a high disinfectant and antiseptic power for killing bacteria, fungi, mycobacteria, spores, mycobacteria, protozoa and viruses.

This nanomaterial is obtained using an impregnation process, which modify the surface thereof and disperse citrus extract particles of 0.3-10 nm in size over said support surface.

Important Factors in the Design of the Support Material

| | |
|---|---|
| Crystalline structure | Crystalline metal oxide |
| Chemical composition | $E/M_aO_{2(c)}(OH)_v(PO_4)_w(SO_4)_x Cl_y(NH_2)_z$ where E is an extract complex solution; M is metal |
| Grain, particle or crystal size | Distribution from 0 to 100 nm |
| Surface | 50 m$^2$/gr |

Extraction of Herbal and/or Fruit Active Agents

The production of extracts involves two steps. First, the ethanolic step where seeds, leaves, peels and shells of selected fruits, said fruits being grape, tangerine, orange, grapefruit, lemon, guava, among other plants, are placed in contact with at least 70% ethyl alcohol solution under constant stirring between 100 and 400 RPM, at a temperature between 30 and 50° C., for a period of time between 24 and 48 hours. The alcoholic portion is removed from the extract by filtration.

Figure 1:
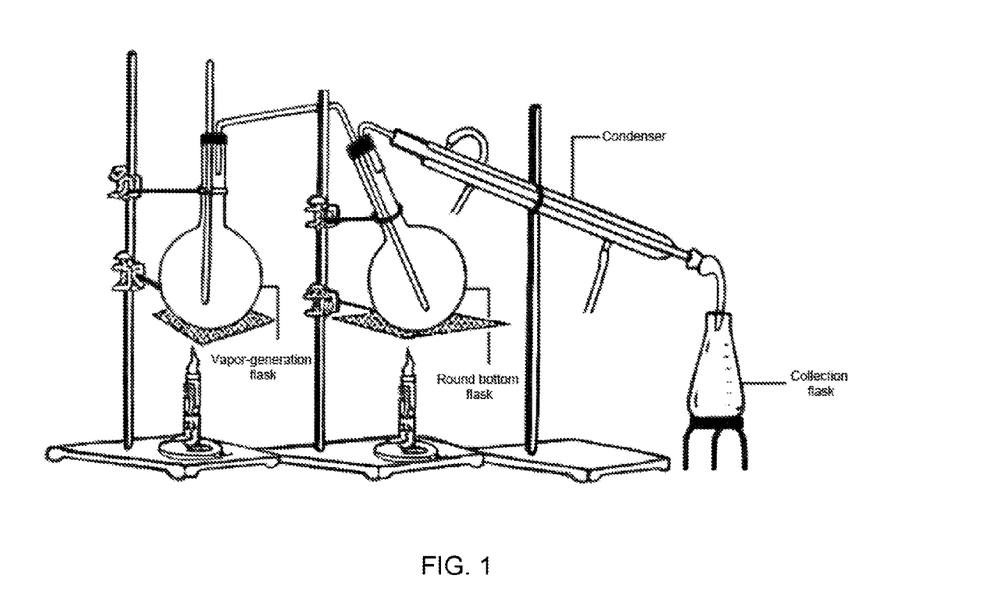
FIG. 1. Extraction system of herbal and fruit active agents and organic oils.

The herbal residue collected from the ethanolic step in a system such as that shown in FIG. 1 where distilled water is placed in the first flask and heated to between 100 and 130° C. The vapor generated is transferred through a tube to another flask wherein herbal residue is place and maintained hot between 40 and 60° C. Vapor is collected on the outlet of the second flask in a condenser with circulating cold water at a temperature between 10 and ° C. The resultant liquid is mixed with that obtained in the first step.

The mixture is allowed to stand at room temperature for 12 hours. The resultant liquid must be of variable color, depending on the plants and fruits used, non-viscous, with an intense bitter flavor and pH from 2 to 5.

Functionalization of the Support

The process for functionalizing the support was improved in order to include extracts.

Significant aspects of said nanomaterial are the chemical characteristics thereof. First of all, the aspect that characterizes the invention as nanotechnology, which is one of its major attributes and an advantage for removing microorganisms, is that it has a particle size between 1 and 100 nm and a crystalline structure, which is as well important since the material's oxygen atoms must be on the outside of the crystal allowing for the access or addition process of functional groups as well as extract adsorption.

As a starting process it is required to prepare solutions providing hydroxyl, phosphate, sulfate, chloride, amino, methyl, and phosphate functional groups at a concentration of 1.4%. For said solutions the following solutes are used:

TABLE 1

Functional groups precursors providing selectivity properties to the nanomaterial.

| hydroxyl | phosphate | sulfate | chloride | amino | methyl | folate |
|---|---|---|---|---|---|---|
| Water | Sodium phosphate | Sodium sulfate | Sodium chloride | ethyl amine | Methanol | Folic acid |
| Ethanol | Phosphoric acid | Sulfuric acid | Hydrochloric acid | Gamma-amino-butyric acid | Formic acid | Pteroyl glutamic acid |

The industrially pre-manufactured titanium dioxide nanomaterial purchased from the chosen provider, preferably Degussa P25, which meets the surface area characteristics of 50 m$^2$/g and particle size between 1 and 100 nm, is placed in a flask with water in a oxide-water ratio of 1:200. Agitation is set to constant speed between about 100 and 400 RPM, and from that point temperature is maintained between 30 and 100° C. Agitation and temperature must be maintained within these ranges for the whole process.

Previously prepared solutions are completely added drop wise one at a time, in the order as recited, maintaining agitation of the overall suspension between about 100 and 400 RPM. Once the addition of one solution is completed the next solution should be added after a waiting time of 5 to 30 minutes. The waiting time is in order to allow the complete adsorption of each functional group to the material surface before the addition of the next solution.

Then it is allowed to dry at temperatures between 30 and 100° C. in order to remove any remaining liquid.

Adsorption of Extracts

In order to realize the incorporation of extracts, the oxide to be used should have a surface area greater than or equal to 50 m$^2$/g.

Extracts added to the support can be from different parts of a plant such as flowers, buds, seeds, leaves, bark, grass, wood, fruit and roots; as well as from different plants such as citruses, grapes, pomegranate, barks like cinnamon and seeds like pepper, leaves like oregano, and many other plant extracts, which have proven to possess antimicrobial properties.

An aqueous solution of 70% extracts is placed in a flask under constant stirring at a speed of between about 100 and 400 RPM, then it continues at a temperature between 30 and 50° C., and the previously treated titanium dioxide nanomaterial is added slowly so as to incorporate the functional groups from the previous process, and stirring is maintained at a speed of between about 100 and 400 RPM for 24 hours.

70% of said solution is comprised of an equitative mixture of extracts from at least three herbal or fruit sources, for example tangerine, grapefruit, orange and lemon.

Characterization Tests

In these exemplary tests titanium oxide was used as a support.

Figure 3:
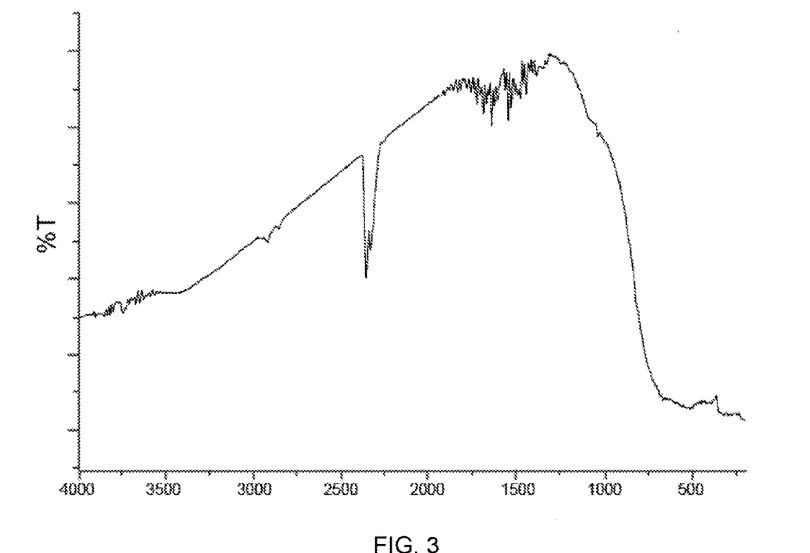
FIG. 3. Infrared spectrum of the titanium dioxide nanomaterial.
Figure 4:
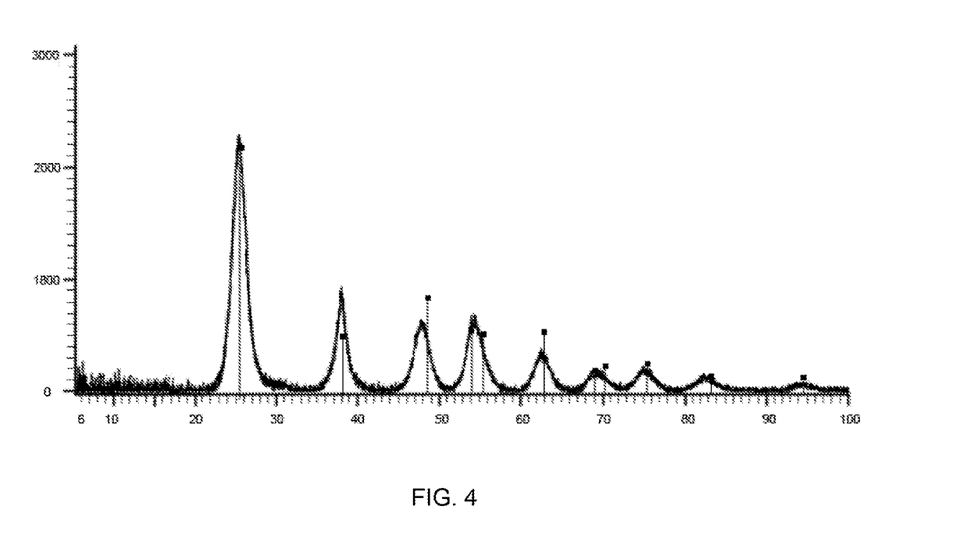
FIG. 4. X-ray diffraction spectrum confirming presence of the anatase phase of titanium dioxide.
Figure 5:
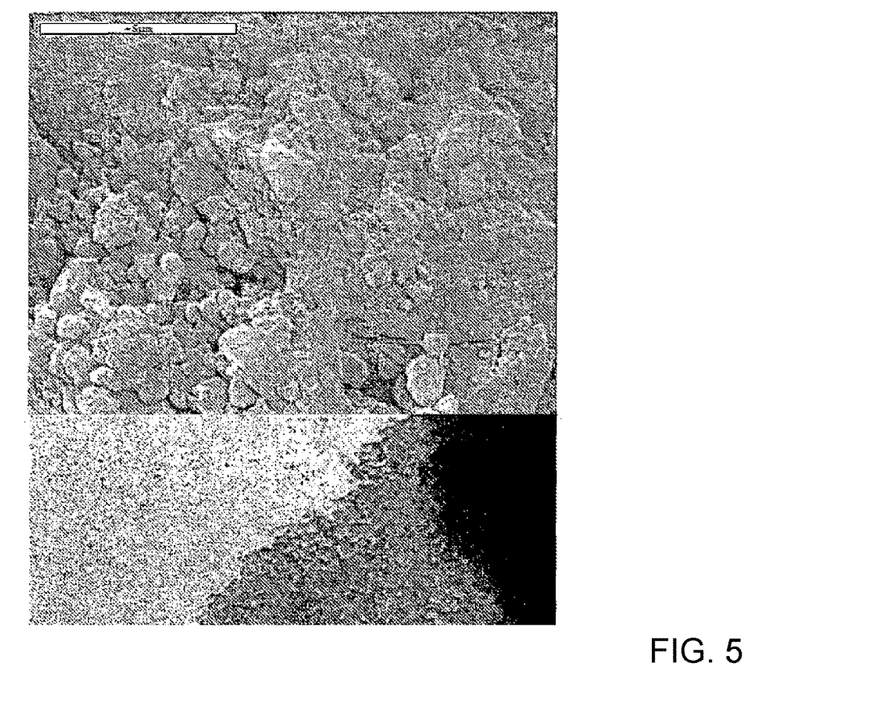
FIG. 5. Electron microscopy confirming particle size.

The infrared transmittance spectrum shows a central band at 3667 cm$^{-1}$. This band is attributed to OH stretching vibration. Generally, this band is observed at 3700 cm$^{-1}$ with pure titanium dioxide, and it is due to the presence of terminal hydroxyl groups, which because of OH stretching vibrations, leads to both Lewis and Brönsted acidic sites. The corresponding OH bending vibrations are centered at 1633 cm-1. Infrared bands associated with stretching vibrations of amine groups were observed at 3230 cm$^{-1}$. These observations are consistent with the fact that the complex could have lost only one atom and probably some decomposition of said complex have occurred as a result of any TiO. Within the spectrum low energy region a centered wide band is observed at 1095 cm$^{-1}$ with a shoulder at 1228 cm$^{-1}$. These bands are due to stretching vibrations (—O—Si—O—). The nanomaterial has several characteristics as observed from the infrared spectrum. In particular, a centered HNH deformation band at 1548 cm$^{-1}$ and an asymmetric stretching band at 3230 cm-1 are evident. The UV-Vis spectra and thermal analysis show that when citrus extracts are adsorbed on the nanomaterial surface the decomposition and evaporation temperatures thereof increase, which means that extracts are protected from ambient factors, thus lengthening its useful life as well as extending its usage or storage range. The infrared profile is shown in FIG. 3, and the X-ray diffraction spectrum confirming presence of the anatase phase is shown in FIG. 4.

Said material has disinfectant and antiseptic properties so it can be used in cleaning, disinfection, antiseptic and healing products. To these ends, it can be included in diverse formulations, which can comprise:

| Ingredient | Minimum value (%) | Maximum value (%) |
|---|---|---|
| Nanoparticulate material | 0.0001 | 40 |
| Soft water | 10 | 98 |
| Sodium lauryl sulfate | 10 | 70 |
| Sodium lauryl ether sulfate | 10 | 70 |
| Ammonium lauryl sulfate | 10 | 70 |
| Ammonium lauryl ether sulfate | 10 | 70 |
| Monoethanolamine lauryl sulfate | 10 | 70 |
| Sodium lauryl ether sulfosuccinate | 10 | 70 |
| Triethanolamine lauryl sulfate | 10 | 70 |
| Decyl polyglycoside | 10 | 70 |
| Alkyl polyglycoside | 10 | 70 |
| Cocoamidopropyl betaine | 10 | 70 |
| Coconut fatty acid diethanolamine | 10 | 50 |
| Polyethylene glycol | 10 | 10 |
| Propylene glycol | 10 | 40 |
| Ethylenediaminetetraacetic acid (EDTA) | 10 | 10 |
| Citric acid | 10 | 20 |
| Sodium chloride | 10 | 30 |
| Glycerin | 10 | 50 |
| Mineral oil | 10 | 50 |
| Coconut palm oil with ethylene oxide | 10 | 50 |
| Stearic acid | 10 | 70 |

-continued

| Ingredient | Minimum value (%) | Maximum value (%) |
|---|---|---|
| Acrylate/acrylamide copolymer | 10 | 40 |
| Polysorbate 85 | 10 | 40 |
| Sodium acrylate copolymer | 10 | 20 |
| Sodium acrylomethyl taurate copolymer | 10 | 20 |
| Trideceth 6 | 10 | 20 |
| Polyacrylic acid | 10 | 20 |
| Triethanolamine | 10 | 20 |
| Xanthan gum | 10 | 20 |
| Guar gum | 10 | 20 |
| Fragrance | 10 | 20 |
| Flavor | 10 | 20 |
| Egg yellow | 0 | 0.1 |
| Red #6 color | 0 | 0.1 |
| Rhodamine color | 0 | 0.1 |
| Lemon pop yellow | 0 | 0.1 |
| Aniline blue | 0 | 0.1 |
| Emerald green | 0 | 0.1 |
| Orange yellow | 0 | 0.1 |
| Blue #1 | 0 | 0.1 |
| Green #5 | 0 | 0.1 |
| Yellow #5 | 0 | 0.1 |
| Green #8 | 0 | 0.1 |
| Violet Woll | 0 | 0.1 |

Testing of Virucidal Activity

Cell Cultures

MDCK cell line cultured on 25 cm$^2$ flasks with minimum essential medium (MEM) (Gibco/BRL, NY, USA) supplemented with 10% bovine fetal serum (Invitrogen, Mexico D.F.) and antibiotics (penicillin 100 IU/mL, streptomycin 100 mg/mL and amphotericin B 10 mg/mL) (Sigma-Aldrich, Inc., St. Louis M. USA) at 37° C. with 5% $CO_2$ are used. Cells must be allowed to grow to 80% confluence.

Virus Titration by Hemagglutination Assay (HA)

Inside test tubes or on V-well plates, dual dilutions of a virus-containing sample are mixed together, with a constant suspension of erythrocytes (use generally 10,000,000 cells/mL), and then incubated. In order to evaluate the result, the amount of cells added are quantified using a spectrophotometer, the last dilution showing complete hemagglutination (HA) is considered as the limit dilution and expressed as hemagglutinating units (HAU's).

Preparation of Erythrocytes

Erythrocytes from chickens of 3 to 5 days of age are used. Chickens are euthanized by blood extraction; the blood is placed in Alsever's solution. Cells are washed several times by centrifugation at 1800×g for 5 min, once supernatant becomes clear it is removed and cells are adjusted to 10% in PBS. When using the solution it is adjusted to 0.5% in PBS.

Titration of Hemagglutinin

Each virus batch must be titrated. Dual dilutions of 1:10 to 1:2560 are made by placing a volume of 0.05 mL of each dilution in wells of 96-V-bottom-well plates. One well for erythrocytes as control must be included.

Erythrocyte suspensions are added to each well with gentle mixing so as not to rupture the erythrocytes. They are incubated at room temperature for 1 to 2 hours.

HA titration is determined by reading the highest dilution capable of agglutinating the erythrocytes.

The titration is reported as the reciprocal of the highest dilution capable of agglutinating the erythrocytes. And it is interpreted as hemagglutinating units: HAU/0.05 mL virus.

Determination of Virus Titration to be Used

The amount of viruses that is needed for testing as well as the effect of the sanitizer on cells is standardized. The solution of titanium dioxide nanomaterial with herbal or fruit extracts adsorbed on the surface thereof is used at the recommended dilution from the sanitizer container (prepared by pouring 75 mL in 5 liters of water). 40 µl of virus are admixed to dilution at different HAU (40, 20 and 4 HAU) and incubated at different points of time: 1, 5 and 15 minutes. Mixtures from each interaction time (virus-nanomaterial) are inoculated with confluence monolayers of MDCK cells, and incubated for two hours at 37° C. under humid atmosphere and 5% $CO_2$. Thereafter, the viral inoculum is removed, fresh culture medium without fetal bovine serum is added, and the monolayers are incubated for 24 hours.

Effect of the Titanium Dioxide Nanomaterial with Herbal or Fruit Extracts Adsorbed onto the Disinfectant Surface Thereof on a Viral Infection MDCK cells are cultivated on 24-well plates until confluence. Different volumes of the sanitizing solution mixed with a constant infective dose of virus are employed. These are incubated for 10 to 15 min at room temperature and then inoculated with confluent cell monolayers on the microtitration plates for two hours.

Then, the sanitizing solution and virus mixture is removed, washed with sterile PBS (pH 7.45), and 1.5 mL of 2.0% methylcellulose in MEM is added to each well so as to incubate again at 37° C. with 5% $CO_2$ until lytic plates are formed (maximum 10 days). The methylcellulose is removed, washed again, 200 µl of 75% methanol is added, then removed after 20 min and the 1% violet crystal is added for 15 min. Then it is washed with tap water, examined, and lytic plates are counted under the microscope. The minimum dose of sanitizing solution is calculated according to the virus cytopathic ability. Virus without sanitizing solution is used as an infective control and uninfected cells are used as negative controls. Since it is a qualitative test, an approximate percentage of reduction of plates formed is calculated.

With these tests, it has been found that the subject invention of the present description inhibits up to 100% of virus infectivity, such as influenza virus, within 0 to 5 minutes.

Testing of Bactericidal and Fungicidal Activity

For laboratory analysis and sample retention, randomly select a product representative subsample to be analyzed, and record the lot number.

To determine the antimicrobial activity, only one method is used, based on determining the reduction percentage of a given number of microorganisms when in contact with a germicide under specific test conditions.

Preparation of Solutions 0.25 M Phosphate Buffer Solution

In a 1000 mL volumetric flask, dissolve 34 g of potassium monobasic phosphate in 500 mL of water, adjust pH between 7.1 and 7.3 with sodium hydroxide solution, bring to volume with water, mix and divide into 100 mL portions. Sterilize in autoclave at 394° K (121° C.) for 15 min, allow to cool, and keep under refrigeration.

Diluted Phosphate Buffer Solution

Place 1.25 mL of 0.25 M phosphate buffer solution into a 1 L volumetric flask and bring to volume with water, mix, and divide into 9 mL and 99 mL portions in test tubes and flasks respectively, sterilize in autoclave at 394° K (121° C.) for 15 min.

Concentrated Neutralizing Solution

Admix 40 g of azolecithin with 280 mL of polysorbate 80 mL and 1.25 mL of phosphate buffer solution, dilute with water to obtain 1 L; adjust pH to 7.2 with the sodium hydroxide volumetric solution or hydrochloric acid volumetric solution, then distribute into 100 ml portions. Sterilize in autoclave at 394° K (121° C.) for 20 min.

Diluted Neutralizing Solution

Mix 100 ml of concentrated neutralizing solution with 25 ml of 0.25 M phosphate buffer solution, add 1675 ml of water, mix together and distribute into 9 ml portions in 20 mm×150 mm threaded test tubes. Sterilize in autoclave at 394° K (121° C.) for 20 min.

Preparation of Culture Media

Prepare and sterilize culture media according to the manufacturer instructions on the product label. In the case of agar culture media for the standard method with neutralizing solution and before sterilizing, add 25 mL of neutralizing solution to one liter of agar culture media for the standard method.

Neutralizing Broth

Mix together the components shown in table 1, heat until dissolution occurs, adjust pH to 7.2, put in autoclave and sterilize at 394° K (121° C.) for 15 min.

TABLE 1

| Components of neutralizing broth | |
|---|---|
| Tryptone | 5.0 g |
| Yeast extract | 2.5 g |
| Dextrose | 10.0 g |
| Sodium thioglycolate | 1.0 g |
| Sodium thiosulfate | 6.0 g |
| Sodium bisulfite | 2.5 g |
| Polysorbate 80 | 5.0 g |
| Soy lecithin | 7.0 g |
| Bromocresol purple | 0.02 g |
| Distilled water | 1 L |

Test Microorganisms and Culture Media

*Staphylococcus aureus* (EMB agar)
*Escherichia coli* (EMB agar)
*Pseudomona aeruginosa*
*Salmonella* sp (EMB agar)
*Enterobacter* sp (E.M.B. Agar)
*Klebsiella pneumoniae* (EMB agar)

*Candida albicans* (EMB agar)
*Aspergillus niger* (EMB agar)

Sample Preparation and Conditioning

Preservation of Test Microorganisms

Preserve microorganism strains by weekly reseeding in 16 mm×125 mm test tubes with inclined culture media (7 ml nutritive agar), incubate for 20 hr to 24 hr at a temperature of 308° K to 310° K (35° C. to 37° C.) and keep under refrigeration.

Preparation of Test Microorganism Suspension

Before testing, make two reseedings of each test microorganism and incubate for 20 to 24 hr at a temperature of 308° K to 310° K (35° C. to 37° C.).

From these cultures, reseed each test microorganism in 22 mm×175 mm test tubes each containing 12 mL of inclined nutritive agar and incubate at the indicated conditions.

Remove growth from each tube with 3 mL of saline solution, transfer the supernatant to a sterile test tube and continue dilution with the same solution until obtaining a suspension with readings between 3% and 5% transmittance at a wavelength of 580 nm.

Determine the CFU number/mL in the suspension and indicate the percent transmittance of a suspension containing 75 to 125×108 CFU/mL. The latter is verified according to the previsions of the Mexican Official Standard NOM-092-SSA1 (see 2 references) and these values are taken into account for future analyses.

Determination of Initial Viable Count

To an Erlenmeyer flask containing 99 mL of sterilized diluted phosphate buffer solution, transfer 1 mL of the test microorganism suspension and make the necessary decimal dilutions in order to obtain plates containing between 25 and 250 colonies each.

Place in sterilized Petri dishes, 1 ml of each dilution in duplicate, add to each plate 15 mL to 18 mL of agar for standard methods, homogenize and allow to solidify, turn the Petri dishes over and incubate for 48 h at 303° K-308° K (30° C.-35° C.). Count colonies contained in each dish in a colony counter.

Procedure

1. Strain seeding and culturing;
2. Determination of surviving cells;
3. Sample preparation;

If necessary, make an appropriate dilution with water to reach product's concentration as recommended by the manufacturer on the package label.

4. Sample inoculation

For each test microorganism, measure precisely and in duplicate 99 mL of the product or its dilution, transfer to 250 mL sterilized Erlenmeyer flasks with screw caps.

Agitate flasks, stop agitation just before inoculation, so that the residual liquid still have motion to facilitate incorporation of the inoculum. Individually inoculate each flask with each test microorganism in the center of the liquid surface, avoiding contact of the pipette with the neck or walls of the flask.

Agitate the flask with the inoculated sample inside and exactly 30 seconds after inoculation, transfer 1 mL of the same to a test tube containing 9 mL of the diluted neutralizing solution or neutralizing broth, mix together and transfer in duplicate 1.0 mL aliquots to sterilized Petri dishes, and continue dilution until the necessary dilutions are obtained to form plates containing 25 to 250 colonies, add 15 mL to 18 mL of agar for standard method as a neutralizer to each plate, homogenize, allow to solidify, turn over the plates and incubate for 48 hr at 308° K to 310° K (35° C. to 37° C.).

After the incubation period, count the CFU number in the plates.

Expression of Results

Determination of % Reduction

Average the results from plates of the initial viable count and surviving cells, then calculate % reduction using the following formula:

$$\% \text{ reduction} = 100 - \frac{S \times 100}{V.C.}$$

where:
S are the surviving cells CFU/mL, and
V.C. is the initial viable count.
Report the percentage of reduction obtained on the product sample.

Interpretation of Results

A product labeled as germicide must have a 99.999 percentage reduction of viable count within 30 seconds of contact at the recommended concentration, when the initial viable count is between 75 and 125×108 CFU/mL.

Sporicidal Activity Tests

Effectiveness tests were carried out based on the AOAC 966.04 methodology, where 59 out of 60 replicas against *Bacillus Subtilis* were obtained.

It is important to point out that the tests have been carried out according to NMX-BB-040-SCFI-1999 "METODO GENERAL DE ANALISIS-DETERMINACION DE LA ACTIVIDAD ANTIMICROBIANA EN PRODUCTOS GERMICIDAS" (General method for analysis-determination of antimicrobial activity in germicide products") where, according to said NMX standard 100% of *Escherichia coli, Salmonella paratyphi, Bacillus subtifis, Vibrio cholerae, Listeria monocytogenes, Streptococcos faecalis* and *Saccharomyces diastaticus* were killed in a period of time of 0 to 5 minutes, while the effectiveness was also of 100% according to said NMX within a time interval of 5 to 10 minutes, and 99.995% within a time interval of 0 to 5 seconds for *Aspergillus niger* and *Staphylococcus aureus*, and 100% within a time interval of 10 to 15 minutes and 99.995% within a time interval of 0 to 10 minutes for *Pseudomonas aeruginosas*.

The invention claimed is:
1. A composite nanomaterial comprising:
a) a nanoparticulate metal oxide support,
b) functional groups chemically adsorbed on a surface of the support, and
c) herbal and fruit extracts physically adsorbed on the surface and pores.

2. The nanomaterial of claim 1, wherein said nanoparticulate metal oxide has a mean diameter size between the range of about 1 nm and about 100 nm.

3. The nanomaterial of claim 1, wherein the functional groups are hydroxyl, phosphate, sulfate, chloride, amino, methyl, folate and impart material selectivity properties towards pathogenic microorganisms.

4. A method for preparing a titanium dioxide nanomaterial with herbal or fruit extracts adsorbed thereon, the method comprising:
   a) preparing herbal and fruit extracts,
   b) modifying said surface by chemical adsorption of functional groups,
   a) physically adsorbing herbal and fruit extracts.

5. The method of claim 4, wherein the extracts can be from barks, stems, roots, leaves, peels, pulp and seeds of citrus plants and fruits.

6. The method of claim 4, wherein said modification of the surface is done maintaining a constant agitation at a mean speed in the range of 100 to 400 RPM.

7. The method of claim 4, wherein said modification of the surface is done maintaining a constant temperature within the range of 30 to 100° C.

8. The method of claim 4, wherein said modification of the surface is done by chemically adsorbing functional groups by adding solutions providing hydroxyl, phosphate, sulfate, chloride, amino, methyl, and folate functional groups at a concentration of 1.4% and adding them in the order listed.

9. The method according to claim 8, wherein said modification of the surface by adsorption of functional groups requires a mean settling time, after adding each solution from 5 to 30 minutes in order to adsorb each functional group completely.

10. The method of claim 4, wherein said modification of the surface requires a drying period at a mean temperature ranging from 30 to 100° C.

11. The method of claim 4, wherein said adsorption of herbal and fruit extracts requires the nanomaterial of claim 1 having a surface area greater than or equal to 50 $m^2/g$.

12. The method of claim 4, wherein said adsorption of herbal and fruit extracts requires the extracts obtained to comprise at least 70% of extracts.

13. The method of claim 4, wherein said adsorption of herbal and fruit extracts requires maintaining a mean constant agitation in the range of 100 to 400 RPM.

14. The method of claim 4, wherein said adsorption of herbal and fruit extracts requires maintaining a mean temperature in the range of 30 to 50° C.

15. The method of claim 4, wherein said adsorption of herbal and fruit extracts requires an agitation period of 24 hours.

16. Disinfectant solutions comprising:
   a) the nanomaterial of claim 1,
   b) various proportions of selected raw materials.

* * * * *